United States Patent
Fuhr et al.

(10) Patent No.: US 8,283,132 B2
(45) Date of Patent: Oct. 9, 2012

(54) METHOD AND DEVICES FOR TREATING INDIVIDUAL BIOLOGICAL CELLS

(75) Inventors: Günter Fuhr, Berlin (DE); Hagen Thielecke, Blieskastel (DE)

(73) Assignee: Fraunhofer-Gesellschaft zur Foerderung der Angewandten Forshung e.V., Munich (DE)

(*) Notice: Subject to any disclaimer, the term of this patent is extended or adjusted under 35 U.S.C. 154(b) by 1203 days.

(21) Appl. No.: 11/718,149

(22) PCT Filed: Nov. 2, 2005

(86) PCT No.: PCT/EP2005/011720
§ 371 (c)(1),
(2), (4) Date: Apr. 27, 2007

(87) PCT Pub. No.: WO2006/048256
PCT Pub. Date: May 11, 2006

(65) Prior Publication Data
US 2009/0148880 A1     Jun. 11, 2009

(30) Foreign Application Priority Data
Nov. 5, 2004   (DE) .................. 10 2004 053 596

(51) Int. Cl.
*C12Q 1/02* (2006.01)
*C12N 5/00* (2006.01)
*C12N 15/02* (2006.01)
(52) U.S. Cl. .................. 435/29; 435/449; 435/325
(58) Field of Classification Search .......... 435/29, 435/286.2, 325, 449
See application file for complete search history.

(56) References Cited

U.S. PATENT DOCUMENTS

| | | |
|---|---|---|
| 5,114,854 A | 5/1992 | Bertholdt |
| 5,877,008 A | 3/1999 | Remenyik et al. |
| 6,003,419 A | 12/1999 | Irita et al. |
| 6,537,800 B1 | 3/2003 | Karube et al. |
| 2003/0059936 A1 | 3/2003 | Baumann et al. |
| 2003/0228695 A1 | 12/2003 | Nakamura et al. |
| 2004/0092002 A1 | 5/2004 | Kim et al. |

(Continued)

FOREIGN PATENT DOCUMENTS
DE     3808531 C1     7/1989
(Continued)

OTHER PUBLICATIONS

Thielecke et al. 2005. Gentle cell handling with an ultra-slow instrument: creep-manipulation of cells. Microsyst Technol. 11: 1230-1241.*

(Continued)

*Primary Examiner* — Taeyoon Kim
(74) *Attorney, Agent, or Firm* — Caesar, Rivise, Bernstein, Cohen & Pokotilow, Ltd.

(57) ABSTRACT

The invention relates to a method for treating a biological cell (1) including a cytoskeleton (3) enveloped by a cell membrane (2). The method includes the following steps: the biological cell (1) and a tool (10) are mutually oriented such that the tool (10) comes into contact with the biological cell (1); the tool (10) and the biological cell (1) are displaced in relation to each other; and a gap is formed in the molecular composite of the cell membrane (2) of the biological cell (1). During the displacement of the tool (10), the cytoskeleton (3) of the biological cell (1) has a state of equilibrium. The invention also relates to a cell manipulator for carrying out the inventive method.

17 Claims, 5 Drawing Sheets

U.S. PATENT DOCUMENTS

| | | | |
|---|---|---|---|
| 2004/0107454 A1* | 6/2004 | Wheeler et al. | 800/21 |
| 2004/0152186 A1 | 8/2004 | Kan et al. | |
| 2006/0051735 A1 | 3/2006 | Fuhr et al. | |

FOREIGN PATENT DOCUMENTS

| | | |
|---|---|---|
| DE | 19714987 C1 | 9/1998 |
| DE | 19841337 C1 | 9/1999 |
| DE | 102004005672 A1 | 8/2004 |
| JP | 08290377 A | 11/1996 |
| WO | 9844972 A2 | 10/1998 |
| WO | 2004074426 A2 | 9/2004 |

OTHER PUBLICATIONS

Bausch et al., "Measurement of Local Viscoelasticity and Forces in Living Cells by Magnetic Tweezers", Biophysical Journal, vol. 76, pp. 573-579 (1999).

Geggier et al., "A time-resolved total internal reflection aqueous fluorescence (TIRAF) microscope for the investigation of cell adhesion dynamics", Appl. Phys. A, pp. 505-513 (1999).

Mitchison et al., "Actin-Based Cell Motility and Cell Locomotion", Cell, vol. 84, pp. 371-379 (1996).

International Search Report for PCT/EP2005/011720.

* cited by examiner

METHOD AND DEVICES FOR TREATING INDIVIDUAL BIOLOGICAL CELLS

BACKGROUND OF THE INVENTION

The invention relates to methods for treating a biological cell. Furthermore, the invention relates to devices for carrying out such methods and their uses.

Several methods for the invasive manipulation of biological cells are known from cell biology. For example, a disruption of the cell membrane and/or a penetration into the cell plasma is necessary when introducing an electrode tip into a cell membrane for the "patch clamp"-technique or during the introduction of a cannula into the cell for the removal of nucleic material. These techniques generally have the disadvantage that a gap is produced in the molecular compound of at least the cell membrane with the invasive intervention into the cell, as a result of which the cell is as a rule no longer viable after the particular manipulation. In order to nevertheless retain the viability, only minimal injuries to the cell membrane should be made with the conventional techniques (e.g., in the micrometer range or less). However, this imposes a significant limitation in the ability to apply the conventional techniques.

Another invasive cell manipulation is the fusion of biological cells. In order to carry out a fusion the cell membranes of adjacent cells are disrupted chemically (e.g., by certain substances or with viruses) or electrically (e.g., with a high voltage pulse) and re-melted or healed in such a manner that cell components of the individual cells are contained in a common, closed cell membrane. The conventional fusion techniques have the disadvantage that an exact and defined cell fusion between two predetermined cells is not available. It was previously necessary to expose a plurality of cells to the particular chemical or electrical treatment for cell fusion and to then sort out the desired fusion products from the treated cells. However, false handlings or undesired multiple fusions (e.g., three-cell or four-cell fusions) can occur. However, this is associated with a significant loss of possibly rare or valuable cells.

A method for the gentle treatment of cell material with a plurality of biological cells is known from WO 2004/074426 in which a probe is moved through the cell material in such a manner that the cells are moved by the probe. Injury to the cells is avoided by the control of the probe described in WO 2004/074426. However, invasive interventions into the cells are not provided in this technique.

The invention has the objective of providing improved methods for treating biological cells, in particular individual cells, cell pairs or cell groups, with which the disadvantages of the conventional techniques can be overcome and that feature in particular a protective handling of the cell material, high reliability and precision and a high yield. The invention also has the objection of providing improved devices for carrying out such methods.

SUMMARY OF THE INVENTION

As concerns the method, the invention is based on the general technical teaching that in order to treat a biological cell with a cell membrane that in particular envelopes cytoplasma and a cytoskeleton, the cell and a tool are moved relative to one another and the cell membrane of the cell is disrupted by the action of the tool, wherein the cytoskeleton of the cell being in a stable equilibrium during the relative movement of the tool and of the cell. An invasive intervention into the cell is advantageously realized with the method in accordance with the invention while the cytoskeleton is mechanically in a state in which it is substantially free of external mechanical tensions and in which the structural and functional relationship between the cell membrane and the inner cell components and the functionality of the inner cell components remain preserved. Furthermore, even the cell membrane is in stable equilibrium during the movement of the tool. During and after the invasive intervention into the cell the functionality of the metabolism and therewith the viability of the cell or at least of a part of the cell remain preserved.

The relative movement of the tool and of the cell takes place slowly in such a manner that the cytoskeleton and the cell membrane, that are continuously subjected to a molecular rearrangement process, can adapt at any point in time to the geometric conditions given by the surface of the tool, especially of a work surface of the tool. The components of the cytoskeleton, which contains in particular filaments of the proteins actin and tubulin and the protein myosin and holds the cell nucleus and the other cell components relative to each other, have sufficient time during the movement of the tool for a new arrangement on the cell membrane and/or the work surface of the tool. The method in accordance with the invention therefore makes it possible that during a cell treatment the cell remains closed by the cell membrane or the work surface of the tool. An invasive intervention into the cell is made possible without the occurrence of large, damaging or irreversible cell openings.

The inventors determined that individual adherent cells, although they can basically escape slow effects of external probes on account of their intrinsic movement (see WO 2004/074426), can be deformed up to a disruption of the cell membrane by a slowly moving tool while surprisingly remaining viable. It is particularly advantageous that the treated cell remains closed relative to the environment during the entire manipulation time.

In general, any disturbance of the molecular compound of the membrane constructed in particular by phospholipids and proteins is understood to be a disruption of the cell membrane here, in which molecules that were first arranged in an adjacent manner in the intact membrane are separated from each other by the external action of the tool. The disruption of the cell membrane results in an opening in the cell membrane at which the inner cell components come in contact with the work surface of the tool or other materials in the cell environment such as, e.g., other cells or cell components or other substances.

Every change of location of the tool and/or of the cell that results in a change of the relative coordinates of the tool and of the cell is designated here with the relative movement of the tool and of the cell. Since the method in accordance with the invention is preferably carried out outside of the body of an organism and the cell to be treated is preferably adherently arranged on a substrate, the relative movement is achieved by at least one of the following movements: movement of the tool, movement of the cell, especially with the substrate, and movement of both parts. The movement of the tool can be superposed, especially in addition to the desired movement of displacement and deformation, by a readjustment movement with which an intrinsic movement of the cell on the substrate is compensated. If in the following as a rule the movement of the tool is referred to, this includes all other movements cited here, especially also of the substrate.

According to a preferred embodiment of the invention the movement of the tool takes place at a rate that is less than or equal to the rearrangement rate of the cytoskeleton. This advantageously ensures the above-cited state of equilibrium of the cell. The rearrangement rate designates here the rate at which parts of the cytoskeleton such as, e.g., characteristic filament structures move on account of the continuously occurring molecular rearrangement process of the cell. The rearrangement rate corresponds, e.g., to the rate with which in the case of an adherently arranged cell an outer edge of the cytoskeleton is moved relative to a substrate. The rearrangement rate is a cell-specific value that can be readily determined in a pretrial by a measurement (see, e.g., B. Alberts et al. in "Molekularbiologie der Zelle", Wiely VCH Verlag, Weinheim, 2004; P. Geggier et al. in "Appl. Phys. A", vol. 68, 1999, pp. 505-513; A. R. Bausch et al. in "Biophys. J.", vol. 76, 1999, pp. 573-579; T. J. Mitchison et al. in "Cell", vol. 84, 1996, pp. 371-379".

Advantages for the adjustment of the tool velocity can result in accordance with another embodiment of the invention if the movement of the tool takes place with a rate that is less than or equal to a migration rate of adherent cells on a surface. This migration rate can be determined in a pretrial on the cell to be treated under the concrete working conditions. The inventors determined that the physiological migration rate of the cell is directly related to the above-cited rearrangement rate of the cytoskeleton and thus can be used as a reference value for the tool movement.

The tool is preferably moved with a rate that is less than 500 µm/h, especially less than 300 µm/h. The above-cited conditions for the most interesting cell types such as, e.g., fibroblasts, macrophages or cancer cells are advantageously met in this rate range so that, e.g., pretrials or tabular values can be dispensed with.

If according to another advantageous embodiment of the invention the biological cell is arranged on the solid surface of a plane substrate and the tool is moved relative to the substrate, advantages can result for the cooperation of the tool and of the substrate. The solid surface forms a support for producing a counterforce during the advance movement of the tool.

The advance movement of the tool relative to the substrate preferably comprises at least one of two phases by which the formation of the structure is positively influenced during and after the cell treatment in accordance with the invention. In an approach phase the tool is moved to the substrate and the cell deformed and constricted between the tool and the substrate. In a translation phase the tool is moved substantially parallel to the surface of the substrate. In this phase the rearrangement of the cell membrane is furthered.

The cited movement types corresponding to the approach phase and the translation phase can be realized in accordance with the invention individually, successively in combination or simultaneously in combination. For example, during the movement in accordance with the approach phase (reduction of the tool-substrate distance) a separation of the cell into at least two cellular bodies as in a punching procedure is provided. The cell treatment in accordance with the invention can furthermore comprise, e.g., only a movement of the tool parallel to the substrate surface. For this, the tool is first set adjacent to the cell to be treated on the substrate surface. The tool touches an edge of the cell when set down or after a first thrusting movement and is then moved through the cell in accordance with the method of the invention, during which the cell is divided into, e.g., two cellular bodies. The substrate surface advantageously forms a guide for the tool movement in this embodiment of the invention.

The cell membrane and with it parts of the cytoplasm and of the cytoskeleton are preferably subjected during the movement of the tool to a deformation, compression and/or elongation. This can advantageously stimulate the disruption of the cell membrane with the formation of new forms of the cell or of the cell components after the invasive intervention.

It is particularly preferred if a healing of the disruption of the cell membrane takes place during and/or after the invasive intervention into the cell membrane so that the cell membrane remains closed or is closed. The healing can take place as a spontaneous healing in that when the tool is at rest the cell membrane closes under the action of surface tension, or it can be furthered by a directed movement of the tool. The cell is advantageously closed by the healing and thus continues to be viable even without the contact with the work surface.

If the inner space of the cell is materially separate from the environment during the formation of a gap and the following healing of the cell membrane an undesirable or non-reproducible change of the structure and function of the cell, especially of the metabolism and of the genetic material can be avoided, which advantageously has a positive influence of the further usage of the cell for purposes of cultivation or of measurements.

Alternatively, it can be provided in accordance with the invention that a foreign substance such as, e.g., a marker substance is introduced into the cell during the formation of a gap.

Other embodiments of the invention are characterized in that the tool remains in contact with the substrate surface after the treating of the cell, e.g., after the division of the cell into at least two cellular bodies. A tool used for separation rests on the substrate surface so that a mechanical wall is advantageously formed between the cellular bodies.

An especially important feature of the invention for using the method in accordance with the invention in cellular biology consists in that the cell membrane has another form, composition and/or size after the healing than before the formation of the disruption. These changes make it possible that investigations and/or changes to the cell can be performed in a defined and reproducible manner.

For example, it can be provided that the cell is divided after the healing into at least two cellular bodies that each have a topologically closed form. The method in accordance with the invention results in a constriction of the cell so that the separate cellular bodies are formed. The cellular bodies can be used as starting materials for further cultivations, treatings or investigations and have the advantage that they are separated from a common precursor cell. It is especially preferable if one of the separate cell bodies is without a nucleus. In this instance the particular other cell body with the cell nucleus is completely viable whereas the cell body without a nucleus can also show metabolic activities as long as ATP is produced by the mitochondria contained in it. The cell body without a nucleus can subsequently be subjected, e.g., to an investigation in order to determine material properties of the other cell body without intervening directly in it.

Alternatively, it can be provided, e.g., that the cell membrane forms with a foreign cell membrane of another biological cell at least one topologically closed cell body after the healing. Thus, the surface of the (first) treated cell can be advantageously modified with substances or structures of the surface of the second cell, e.g., in order to present certain antigens or marker substances on the first cell. The fusion or pair formation of cells in which the first cell is fused with at least one other cell is particularly preferred in this case. The cell fusion in accordance with the invention has the particular advantage over the conventional fusion methods that the above-cited false handlings or possibly undesirable multiple fusions can be avoided and even rare or particularly valuable cells such as, e.g., stem cells can be fused in a purposeful manner with a practically 100% yield. A preferred application of the cell fusion in accordance with the invention is also present in the hybridoma technique for producing monoclonal antibodies.

Further advantages for the ability to control and reproduce the modification of the first cell with material from a foreign cell, especially in cell fusion, can result if the cells are arranged overlapping each other at least partially and in particular superposed over each other on a substrate during the treatment with the tool.

As concerns the device the above-cited objective is solved by a cell manipulator that comprises in particular a tool for treating individual biological cells with at least one work surface with which the cell membrane of the cell can be locally and selectively deformed, and has a drive device with which the tool can be moved in such a manner that the cytoskeleton of the cell is in a mechanically stable equilibrium during the action of the tool on the cell. Precise and reproducible invasive interventions in the cell can be advantageously realized in accordance with the method of the invention.

The drive device of the cell manipulator in accordance with the invention is especially adjusted for tool advance rates in a range of 0.1 μm/h to 500 μm/h. To this end, a piezoelectric drive or a magnetic drive is preferably provided that facilitates a precise adjusting of such slow tool movements.

According to a preferred embodiment of the invention the work surface of the tool has a characteristic size that is less than the size of the cell, in particular less than the lateral extension of the cell on a substrate. The characteristic size is preferably less than 200 μm, in particular less than 10 μm. The characteristic size of the work surface designates here the extension of the contact surface that forms when the tool touches the cell prior to the movement of the tool. As a result of the miniaturization of the work surface the cell manipulator can be advantageously used for very varied cell types. It is especially preferable if the work surface of the tool has a characteristic size that is less than 1 μm. Even such small work surfaces that are sufficiently stable can advantageously be made available since the movement of the tool takes place substantially without force in the method in accordance with the invention.

The tool and particularly its work surface can advantageously be optimized as a function of the particular application of the invention. According to a variant the work surface is formed in such a manner that the tool has a straight side edge that is oriented during operation parallel to the surface of the substrate. The adaptation of the form of the side edge to the substrate surface is advantageous for an effective cooperation of tool and substrate. According to an alternative variant the work surface can have a structuring with projections such as, e.g., pointed elevations. The structuring on the work surface of the tool facilitates a fixing of the cell on the substrate during the treating of the cell. Finally, the work surface can have a complex form with several partial surfaces that make it possible to divide the cell into more than two parts. The work surface can advantageously form, e.g., a cross shape in order to divide a cell into four cellular bodies.

If the tool carries a coating at least along the work surface that prevents an adhesion of biological cells, this results in advantages for the ability to control the work surface movement since independent cell movements of the cell are prevented by the coating of the work surface.

According to a further modification of the invention the cell manipulator is additionally provided with a positioning device with which at least one of the components drive device and a substrate with the cell can be moved, and/or with a sensor device that serves to detect the position of the tool and/or of the cell to be treated.

An expanded area of application of the cell manipulator can be advantageously achieved if two or more tools are provided that are moved synchronously with a common drive device or separately with separate drive devices.

An independent subject of the invention is constituted by the use of the method in accordance with the invention or of the cell manipulator for cell fusion.

Further preferred applications of the invention are in the diagnosis or characterization of individual cells such as, e.g., in the material analysis of components of the cytoplasma or in an analysis of the genetic material in the individual cell or in tests of the interaction of the individual cell with foreign substances such as, e.g., in the investigation of pharmacological active substances. It is particularly advantageous for the test application that the cell, that is at first uniform, can be divided into different parts that nevertheless constitute a physiologically homogeneous system even after the division and can be exposed to various test and reference substances.

BRIEF DESCRIPTION OF SEVERAL VIEWS OF THE DRAWINGS

Further details on advantage of the invention are described in the following with reference made to the attached drawings, which show in FIGS. 1A to 1D: illustrations of phases of the treatment of a biological cell in accordance with the invention.

DETAILED DESCRIPTION OF PREFERRED EMBODIMENTS

The invention is described in the following with exemplary reference made to preferred embodiments illustrating the usage of a tool having a cutting edge shaped like a wedge or a truncated cone as work surface. It is emphasized that the realization of the invention is not limited to the examples shown but rather, modified in accordance with the above-cited features, can also be realized with other tool forms (see, e.g., FIG. 4). It is furthermore emphasized that the biological cells in the attached drawings are shown only schematically and can have other forms in practice, depending on the cell type. Details of the conventional techniques for cell cultivation and for monitoring cell cultures, e.g., with a microscope, are not described in detail since they are known.

Figure 1:
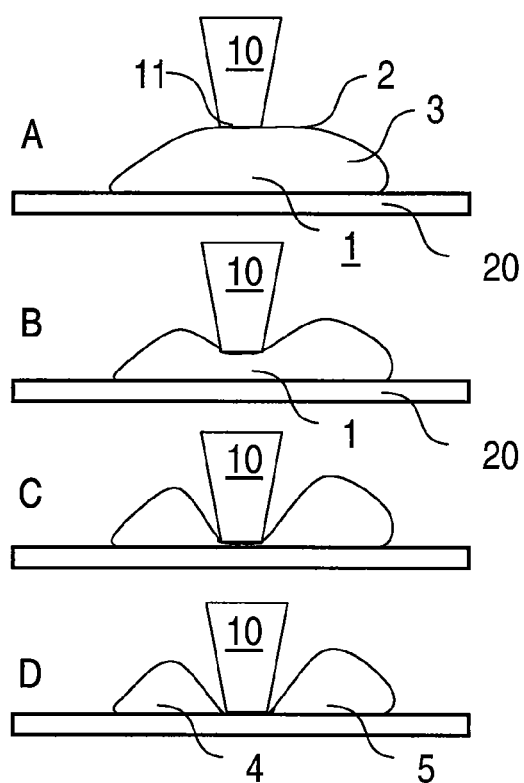

The sequence of a first embodiment of the method in accordance with the invention is schematically illustrated in partial images A to D in FIG. 1. According to FIG. 1A a biological cell 1 is arranged on a substrate 20. The cell 1 has a cell membrane 2 that encloses in particular cytoskeleton 3, that encloses the cell nucleus and other cellular components (not shown). The substrate 20 is, e.g., a culture carrier, e.g., of glass or plastic that is arranged in a culture vessel (not shown) or is formed as a part of the latter. The tool 10 shown in a schematic sectional view has the shape of a wedge whose wide foot, that is uppermost in the figure, is connected via other mechanical components (see FIG. 3) with a drive device and whose lower, free end forms the work surface 11 for acting on cell 1.

In the embodiment of the invention shown in FIG. 1 the tool 10 and the cell 1 are at first oriented in such a manner relative to one another that the work surface 11 of the tool 10 touches the cell membrane 2 from the outside (FIG. 1A). This mutual orientation can be controlled while being visually monitored in a microscope or automated, e.g., with an optical sensor. The tool 10 is subsequently vertically approached with a rate of 20-100 µm/h towards the substrate 20, the cell 1 being deformed (FIG. 1B). The deformation results in the formation of a local impression on the cell surface. The parts of the cell membrane and of the inner cellular components arranged at first in the reduced distance between the work surface 11 and the substrate 20 are increasingly displaced with the progress of the movement of the tool 10. During this displacement the cytoskeleton 3 is in a state of equilibrium. This means that filaments of the cytoskeleton 3 release connections with the cell membrane or mutual connections during the movement of the tool and form them again in adjacent areas in which no displacement takes place. This releasing and subsequent reconnecting of the cytoskeleton (rearrangement) takes place substantially at the same rate as the natural cytoskeleton rearrangement. Therefore, the movement of the tool results at first only in a change of form that, however, is tolerated and compensated by the cell on account of the high form variability of biological cells.

If the distance between the tool 10 and the substrate 20 corresponds substantially to twice the membrane thickness, a constriction occurs between the parts of the cell 1 on both sides of the tool 10 (FIG. 1C). The inventors determined that in this phase the molecular compound of the cell membrane 2 can be gapped without the cell opening to the environment. Instead, the further movement of the tool 10 after the constriction results in a merging of the sections of the cell membrane 2 that contact each other until the work surface 11 of the tool 10 touches the substrate 20 and two separate cellular bodies 4, 5 are formed (FIG. 1D). Both cellular bodies 4, 5 are enveloped by a topologically closed cell membrane and are both viable as long as the metabolism in the particular cell body is supplied with sufficient energy. In the further procedure further manipulations, cultivations or investigations can be carried out on cellular bodies 4, 5 depending on the particular application.

Figure 2:
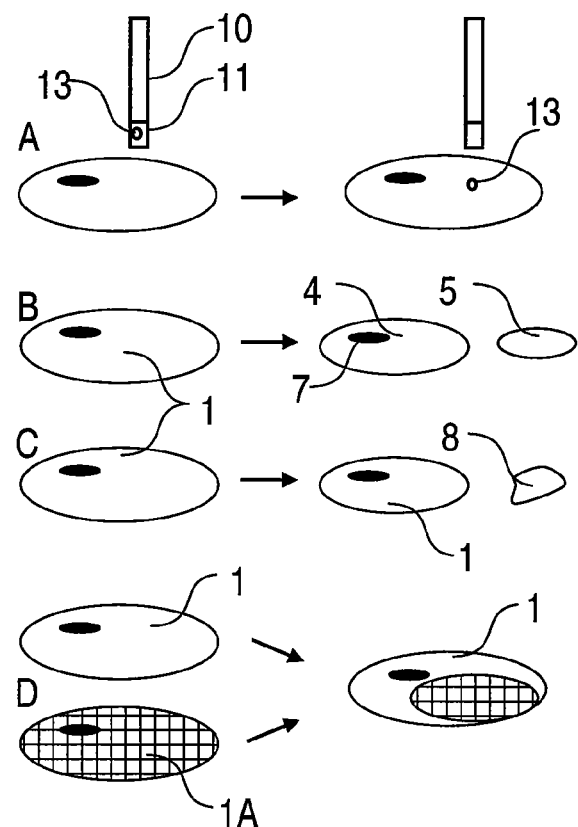
FIGS. 2A to 2C: illustrations of various embodiments of the treatment of biological cells in accordance with the invention.

FIG. 2 illustrates schematically different variants of invasive interventions on biological cells with the method in accordance with the invention. According to FIG. 2A a penetration of the tool 10, on whose work surface 11 a chemical substance 13 is arranged, into the cell 1 is provided. The chemical substance 13 comprises, e.g., a marker substance for fluorescence measurements or a biologically active macromolecule such as, e.g., a DNA segment. The tool 10 is introduced with the substance 13 through the cell membrane of the cell 1 and the substance 13 is given off from the tool into the cytoskeleton at a desired position during a rest phase of the tool 10. The tool 10 is subsequently withdrawn. The course according to FIG. 2A can be modified in such a manner that the substance 13 is deposited in the cell nucleus 7 or that a substance is removed from the cytoplasm or the cell nucleus with the tool.

FIG. 2B shows a course analogous to that of FIG. 1, in which the cell 1 is divided into two cellular bodies 4, 5, each of which has a topologically closed form. The cell body 4 contains the cell nucleus 7 whereas the cell body 5 is without a nucleus.

FIG. 2C illustrates the removal of a sample 8 from the cell 1. The sample 8 comprises, e.g., a section of the cell membrane and/or parts of the cytoskeleton or of the cytoplasm that was removed from the cell 1 with the tool whereas the viable state of the cell 1 remains preserved.

The principle of the fusion in accordance with the invention between different cells 1, 1A is schematically shown in FIG. 2D. The cell membranes of cells 1, 1A, that are arranged adjacent to one another, are opened with a tool with the method in accordance with the invention and melted to a new composite in which a part of the foreign cell 1A is received in the first cell 1 (FIG. 2D) or both are completely merged.

Figure 3:
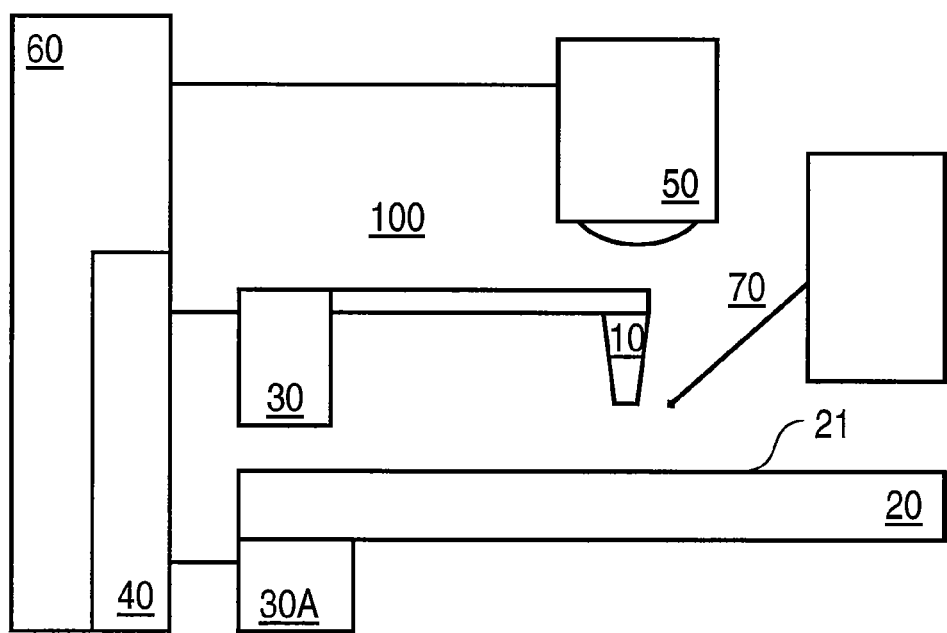
FIG. 3: a schematic view of an embodiment of a device in accordance with the invention for treating biological cells.

The components of a cell manipulator 100 in accordance with the invention are schematically illustrated in FIG. 3. The tool 10 is connected via a mechanical component, such as, e.g., a carrier rod to the drive device 30 that is adapted to adjust the slow displacement movement of the tool 10 relative to a cell (not shown) on the substrate 20. The substrate 20 can also be equipped with a drive device 30A in order to form a slow advance relative to the tool 10. Furthermore, cellular movements of the cell on the substrate 20 can be compensated with the drive devices 30 and/or 30A.

The tool 10 can move with the drive device 30 in all three spatial directions, especially vertically to the surface of the substrate 20 and in a plane parallel to this surface. To this the end drive device 30 can comprise several individual drives that provide the advance movements in the individual spatial directions. The drive devices 30, 30A and/or the individual drives are known piezoelectric drives that are designed to adjust relative rates below 300 µm/h.

The substrate 20 is, e.g., a culture carrier of glass or plastic. A structured coating can be provided on the surface 21, which coating has adhesive areas (islands) in which cells preferably adhere and non-adhesive areas in which the cells do not adhere or adhere with reduced effectiveness. This makes it possible to treat one or several cells while they are on an adhesive island. A cell migration is suppressed by the surrounding non-adhesive areas so that a separate readjustment movement for compensating the cell migration can be avoided.

The tool 10 and/or the substrate 20 can be moved relative to one another in all three spatial directions with a positioning device 40. The positioning device 40 is a known adjusting drive with which a positioning of the tool 10 relative to the cell to be treated is provided.

The reference numeral 50 designates in a general manner an optical sensor device for monitoring the positioning and the displacement movement of the tool 10 relative to the cell. The sensor device 50 is typically part of a light microscope in whose beam path the tool 10 and the substrate 20 are arranged.

The drive devices 30 and/or 30A, the positioning device 40 and the optical sensor device 50 are monitored and controlled by a control device 60. The control device 60 is, e.g., a microcontroller or is contained in a control computer.

Figure 8:
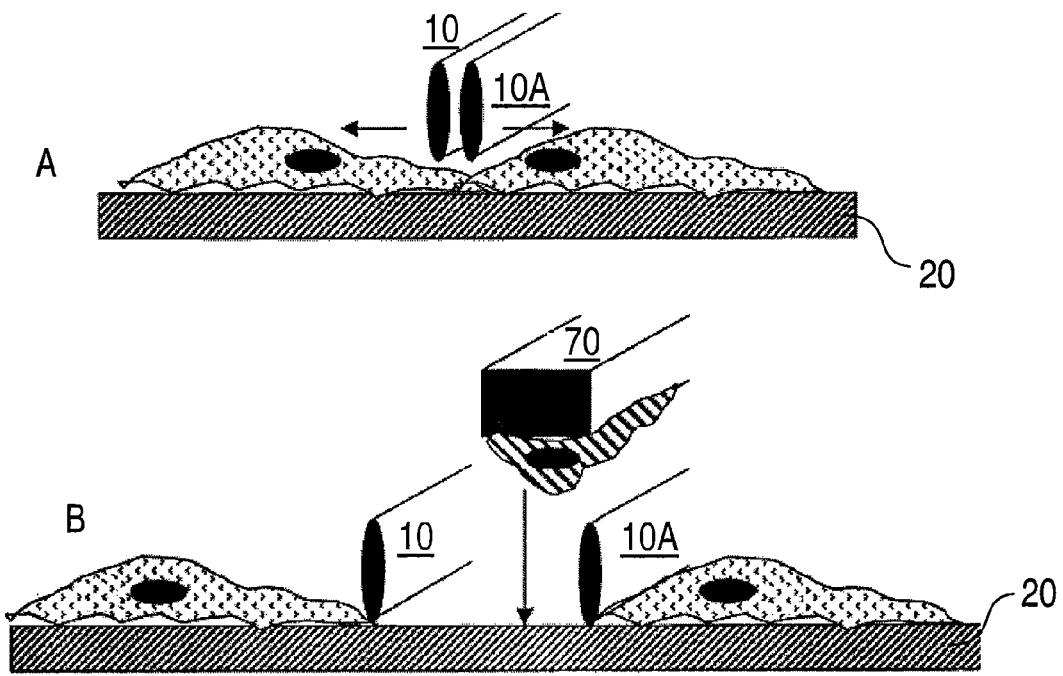

The reference numeral 70 refers in general to an optionally provided further tool that can be actuated, if necessary, independently from tool 10 (see FIG. 8).

Figure 4:
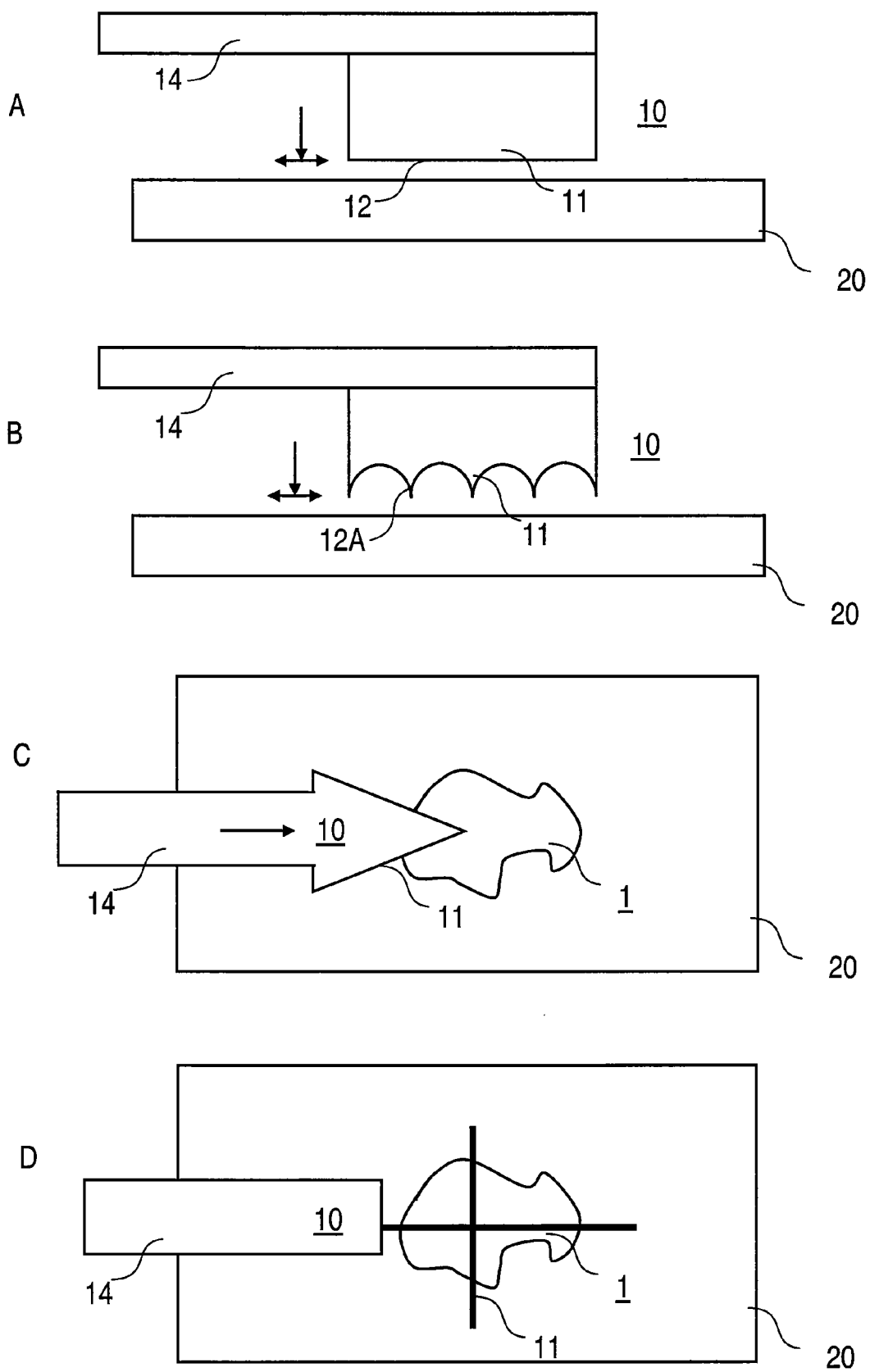
FIG. 4: schematic illustrations of various tool designs.

FIG. 4 shows various designs of the tool 10 of the cell manipulator in accordance with the invention by way of example. The partial images A and B illustrate in a schematic lateral view the tool 10 with the work surface 11 at a slight distance from the surface of the substrate 20. According to partial image A the work surface 11 forms a straight side edge 12 that can be placed on the surface of the substrate 20 and touch it over its entire length given a parallel orientation relative to the substrate 20 and a vertical approach movement. According to the partial image B the work surface 11 is structured in such a manner that no smooth straight side edge is given as in partial image A but rather a structure with a plurality of pointed projections. The projections form several structured, e.g., arched side edge sections 12A under whose action a cell can be separated into two cellular bodies by a translatory movement parallel to the substrate surface.

The tools 10 of the partial images A and B are preferably used in a combined movement in the approach- and translation phases cited above. The length of the side edge 12 is, e.g., 0.5 mm.

The partial images C and D of FIG. 4 illustrate in a schematic top view two other shapes of the tool 10. According to partial image C a wedge-shaped work surface 11 is provided with which the cell 1 can be divided into two cellular bodies on the substrate 20 upon a movement of the tool 10 parallel to the substrate surface (translation phase). According to partial image D the tool comprises a cross-shaped work surface 11 with which the cell 1 can be separated into four parts on the substrate 20 in the course of an approach movement.

The component 14 schematically illustrates in each instance a mechanical structural component (e.g., a carrier rod) via which the tool 10 is connected to the positioning device 30 (see FIG. 3).

Figure 5:
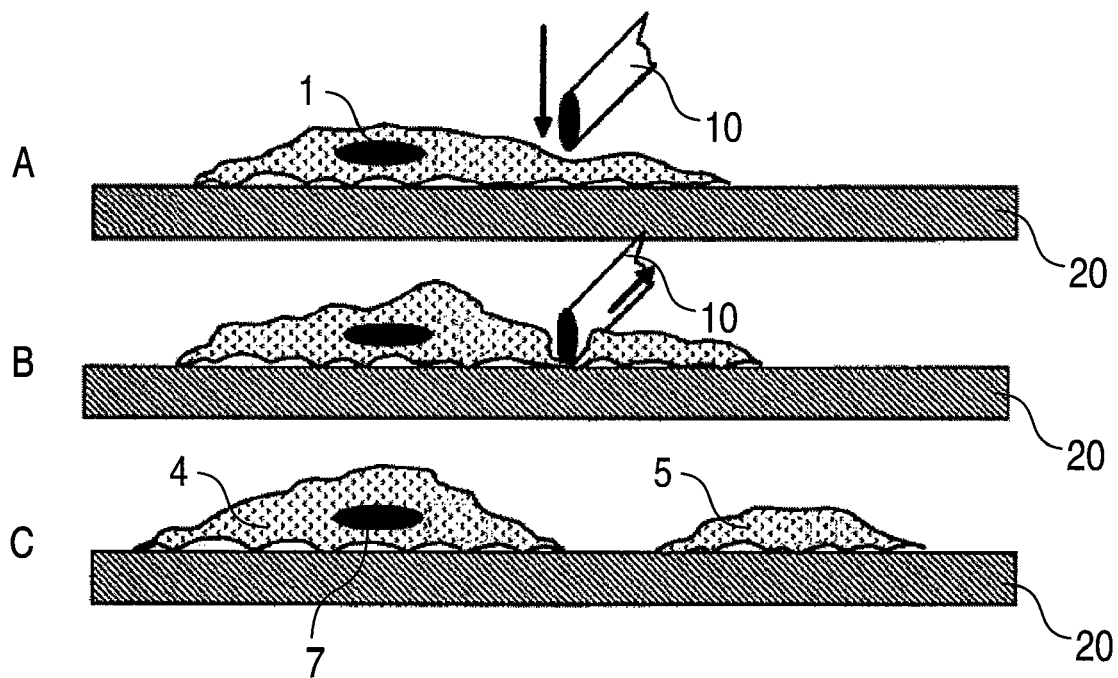
FIGS. 5 to 8: further illustrations of embodiments of the treatment of biological cells in accordance with the invention.

FIGS. 5 to 8 schematically illustrate experimental results that the inventors achieved with the method in accordance with the invention. FIG. 5 shows analogously to FIG. 1 and FIG. 2B and with further details the division of a cell 1 into two cellular bodies 4, 5. According to partial image A an adherent cell 1 such as is typical for in vitro cultures is arranged on the substrate 20. The cell 1 is, e.g., a fibroblast cell or a stem cell adherently arranged on a substrate. The tool 10 is arranged in the direction of the arrow above the cell 1 with the positioning device (40, see FIG. 3). The tool 10 shown in a schematic perspective view is provided with an elongated cutting edge with an elliptical cross section whose surface forms the work surface 11. The invention has the particular advantage that in numerous applications the form of the tool has no significance or significantly less significance for the treatment of cells in accordance with the invention than is the case in conventional techniques with rapid tool movements.

The length of the cutting edge is selected in such a manner that the work surface 11 extends over the entire dimension of the cell 1. On the other hand, the width of the cutting edge is significantly less than the dimension of the adherent cell. It has, e.g., a value of 5 µm as the characteristic size of the work surface. The tool movement comprises two phases. During the approach phase according to FIG. 5A the tool movement takes place along a surface normal of the substrate 20, e.g., at a rate in the range of 5 to 50 µm/h. When the constriction of the cell has been achieved on both sides of the tool 10 (FIG. 5B), the translation phase of the tool movement follows. During this phase the tool 10 is moved parallel to the surface of the substrate 20. The rate of this movement is also selected within a range of 5 to 50 µm/h.

After the melting and the healing of the cell membranes of the two cell parts the separate cellular bodies 4, 5 are present that can even be distanced from one another by independent cell migration (FIG. 5C). The cell body 4 contains the cell nucleus 7 and continues to be vital, capable of movement and can divide with it. The cell body 5 can be used to characterize the original cell by an analysis of the membrane components of the cytoplasma, of cellular organelles and also of genetic material in the cytoplasm such as, e.g., mRNA. The cell components to be investigated can be advantageously separated quantitatively and sufficiently for the particular analysis without a loss of vitality of the cell body 4.

Figure 6:
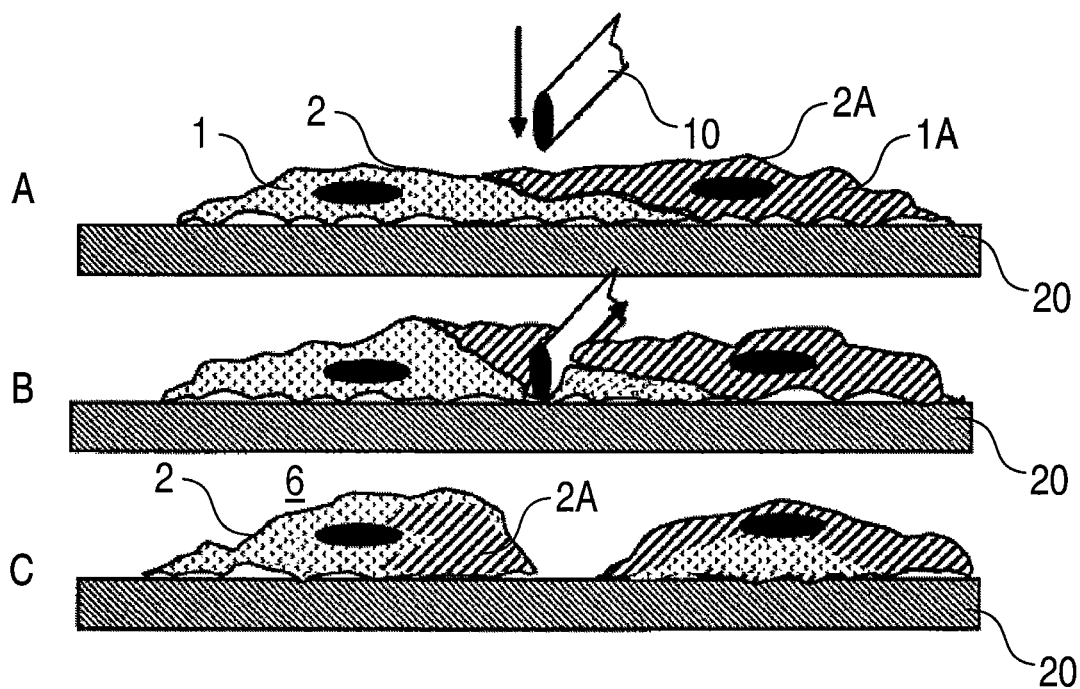

FIG. 6 illustrates a course of a method analogous to that in FIG. 5, in which instance, however, two cells 1, 1A each with a cell membrane 2, 2A are adherently arranged mutually overlapping one another on the substrate 20. Such overlappings frequently occur spontaneously in cell cultures, e.g., when a high cell density is given, or when a so-called feeder cell layer is present on the surface of the substrate 20, as is known from the cultivation technology for stem cells.

According to FIG. 6A the tool 10 is positioned over the overlapping area of cells 1, 1A, subsequently lowered with the above-cited movement rate and optionally moved in a translation phase parallel to the surface of the substrate 20. As a result of the invasive action of the tool 10, the cell membranes 2, 2A are opened and are closed again during the subsequent healing with a correspondingly changed composition and form. As a result, in the fusion cell 6 parts of cell membrane 2A of cell 1A (shown in hatching) are inserted in the cell membrane of cell 1 (shown in dots) and vice versa.

A defined paired fusion of biological cells is possible with the method shown in FIG. 6 such as is desired, e.g., when providing the first cell with antibodies from the second cell.

Figure 7:
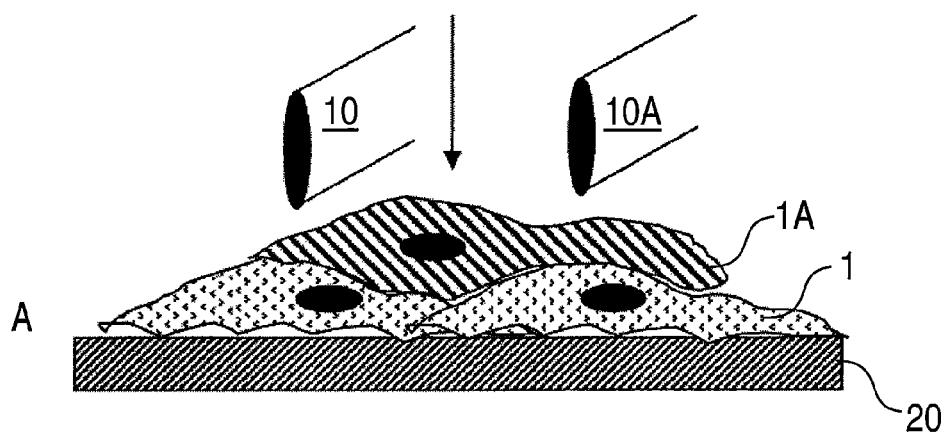

FIG. 7 illustrates a further example of a fusion method using two tools 10, 10A. A monolayer of cells 1 of a first cell type is provided on the substrate 20 on which monolayer one or several cells 1A of a second cell type can be cultivated. This arrangement corresponds, e.g., to the cultivation of stem cells on a feeder cell layer or to the combination of different cell types in so-called tissue engineering.

The tools 10, 10A are slowly pressed in the approach phase into the cell material (FIG. 7A) and are then optionally moved in the following translation phase parallel to the surface of the substrate 20 (FIG. 7B) in analogy with the above-described method. As a result of the simultaneous movement of the tools 10, 10A, in addition to the fusion of the cells 1, 1A, parts of the cell material can furthermore be separated from the fusion cell 6 in the area between tools 10, 10A. To this end, a movement of the tools 10, 10A is provided vertically to the longitudinal extension of the particular work surfaces and parallel to the surface of the substrate 20.

Furthermore, the method shown in FIG. 7 can be modified as follows. The orientation of the tools 10, 10A can be adjusted relative to the cells 1, 1A as a function of the requirements with the optical sensor device, especially a microscope in such a manner that both cell nuclei or only one cell nucleus of one of the cell types is contained in the fusion cell 6. Furthermore, the cells can be pushed together on the substrate 20 with the tools 10, 10A before the fusion takes place. Finally, the cells and especially the fusion cell 6 can be shifted laterally on the substrate 20.

FIG. 8 illustrates a further complex manipulation using two tools 10, 10A that are first lowered into a monolayer of the cells 1 on the substrate 20 and subsequently pushed apart laterally parallel to the surface of the substrate 20 and vertically to the longitudinal orientation of the work surface 11 (FIG. 8A). In this process, a gap is created in the monolayer (cell film). An important advantage of the invention is that the form of this gap can be determined independently of the arrangement of the cells exclusively by positioning and lowering the tools. In distinction to conventional sectioning methods no undesirable wound edges but rather closed, healed membrane forms are formed on the circumferential edge of the gap. Then, one or more cells or an artificial object can be inserted into the gap between the cells 1 with the further work tool 70 (see also FIG. 3). The artificial object can be, e.g., a biological or synthetic filler, a sensor device, a microsystem or a tissue part (e.g., nerve cell compounds or muscle cell compound, endothelia, combinations of them).

Figure 9:
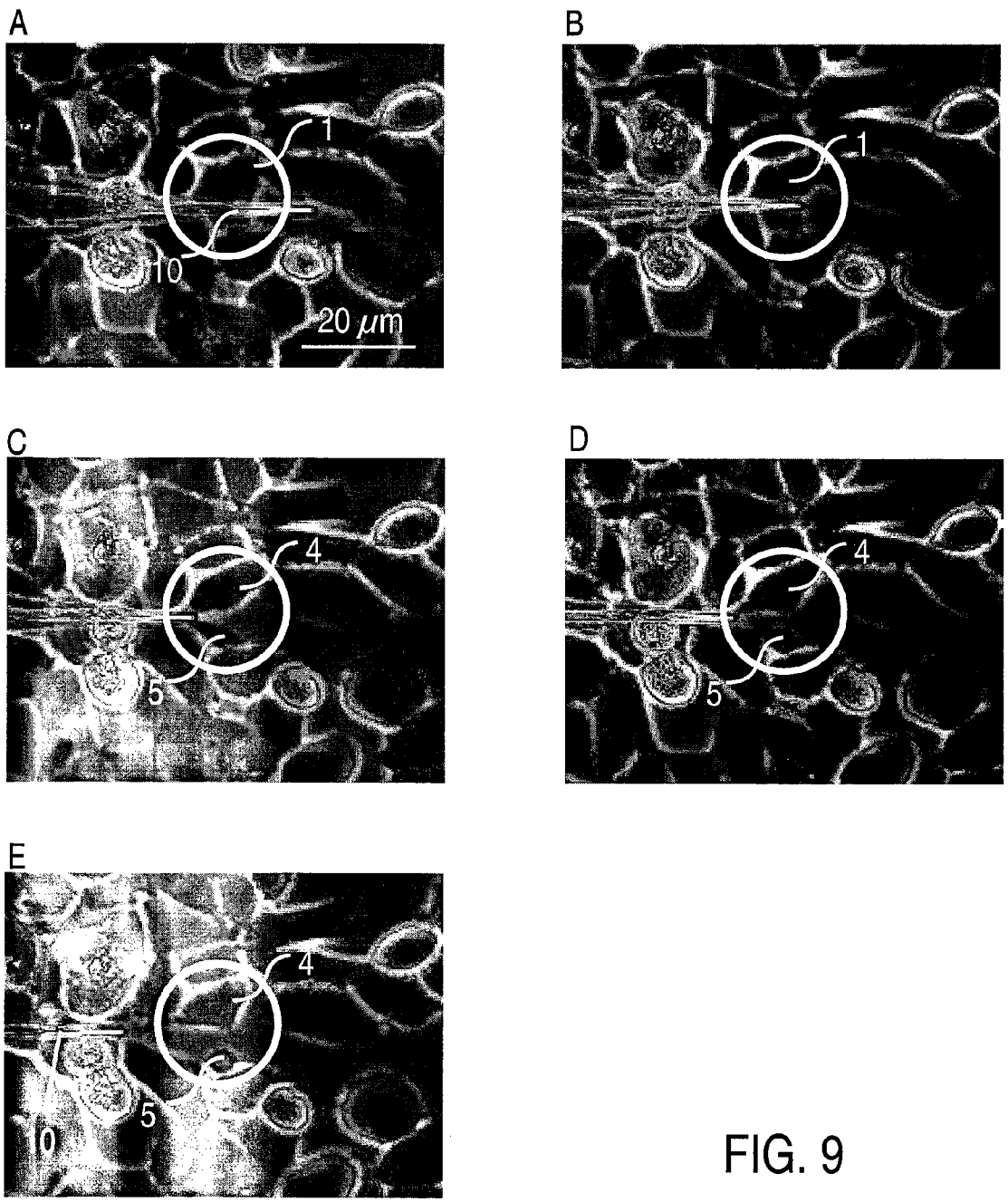
FIG. 9: photographic images that show several phases of a separation in accordance with the invention of a cell into two cellular bodies.

The photographic images A to E in FIG. 9 show the progress of the separation of a cell 1 in accordance with the invention with the tool 10 into two cellular bodies 4, 5 using the example of a concrete experimental result. The presentation shows fibroblast cells on a substrate 20. An elongated glass tip whose diameter is approximately 2 µm on the pointed end is used as tool 10. According to partial image A the tool 10 is first placed on the substrate adjacent to the cell 1 to be treated. The tool 10 is subsequently shifted in accordance with the translatory movement cited above parallel to the surface of the substrate (to the left in the images), wherein a partial and in the further course of the movement and a complete division into cellular bodies 4, 5 takes place in accordance with partial images C and D. Partial image E shows the further mobility of cellular bodies 4, 5 after the division.

The features of the invention disclosed in the above description, the claims and the drawings can be significant individually as well as in combination for the realization of the invention in its various embodiments.

The invention claimed is:

1. A method for treating an individual biological cell that has a cell membrane, a cytoskeleton and inner cell components, said cytoskeleton and inner cell components being enclosed by the cell membrane, comprising the steps:
   providing the biological cell on a solid substrate,
   mutually orienting the biological cell and a treating tool so that the treating tool touches the biological cell,
   moving the treating tool and the biological cell relative to one another, said treating tool having a work surface with a characteristic size that is smaller than a size of the biological cell, and said treating tool being moved relative to the substrate at a rate in a range of 0.1 µm/h to 500 µm/h,
   wherein, during the moving step, the cytoskeleton of the biological cell is in a state of equilibrium, in which the cytoskeleton is substantially free of external mechanical tensions and a structural and functional relationship between the cell membrane and the inner cell components and a functionality of at least of a part of the inner cell components remain preserved, and
   forming a disruption in a molecular compound of the cell membrane of the biological cell, whereby the biological cell is treated, said disruption being formed by the treating tool and the biological cell remaining closed relative to an environment of the biological cell by the cell membrane or the work surface of the treating tool.

2. The method according to claim 1, wherein the rate of moving the treating tool is less than or equal to a rearrangement rate of the cytoskeleton.

3. The method according to claim 1, wherein the rate of moving the treating tool is less than or equal to a migration rate of adherent cells on a surface.

4. The method according to claim 1, wherein the moving of the treating tool relative to the substrate comprises at least one of an approach phase in which the distance of the treating tool relative to the substrate is reduced, and a translation phase in which the treating tool is shifted parallel to a surface of the substrate.

5. The method according to claim 1, wherein the cell membrane is subjected during the moving step to a deformation, compression and/or elongation by the treating tool.

6. The method according to claim 1, further comprising a healing of the disruption so that the cell membrane is closed.

7. The method according to claim 6, wherein there is a separation of an inner space of the cell from the environment of the cell during the forming and the following healing of the disruption in the cell membrane.

8. The method according to claim 6, wherein the cell membrane has at least one of another form, composition and size after the healing than before the formation of the disruption.

9. The method according to claim 8, wherein the cell is separated after the healing into two cellular bodies that each has a topologically closed form.

10. The method according to claim 9, wherein one cellular body of the two cellular bodies is without a nucleus.

11. The method according to claim 10, wherein the cellular body without a nucleus is subjected to an investigation.

12. The method according to claim 8, wherein: (a) the biological cell is fused with at least one other biological cell to form a fusion cell; (b) the at least one other biological cell has a foreign cell membrane foreign to the biological cell; and (c) the cell membrane forms at least one topologically closed cell body with the foreign cell membrane of the at least one other biological cell after the healing.

13. The method according to claim 12, wherein the cells are arranged superposed above one another on a substrate during fusion.

14. The method according to claim 1, further comprising the step of fusing the at least one biological cell with at least one other biological cell to form a fusion cell, said at least one other biological cell having a foreign cell membrane foreign to the at least one biological cell.

15. The method according to claim 14, wherein a cell manipulator is used for treating the biological cell, said cell manipulator comprising:
   the substrate for receiving a biological cell,
   the treating tool for treating the biological cell, and
   a drive device for moving the treating tool relative to the substrate,
   wherein the treating tool has a work surface under the action of which the cell membrane of the biological cell can be locally selectively deformed.

16. The method according to claim 1, further comprising the step of diagnosis or characterization of individual cells after said step of forming a disruption in the molecular compound of the cell membrane.

17. The method according to claim 16, wherein a cell manipulator is used for treating the biological cell, said cell manipulator comprising:
   the substrate for receiving a biological cell,
   the treating tool for treating the biological cell, and
   a drive device for moving the tool relative to the substrate,
   wherein the treating tool has a work surface under the action of which the cell membrane of the biological cell can be locally selectively deformed.

* * * * *

UNITED STATES PATENT AND TRADEMARK OFFICE
CERTIFICATE OF CORRECTION

PATENT NO.         : 8,283,132 B2
APPLICATION NO.    : 11/718149
DATED              : October 9, 2012
INVENTOR(S)        : Günther Fuhr et al.

It is certified that error appears in the above-identified patent and that said Letters Patent is hereby corrected as shown below:

On the cover page at item (73), the assignee information is amended to read as follows:

(73) Assignee: Fraunhofer-Gesellschaft zur
               Foederung der angewandten
               Forschung e. V., Munich (DE)

Signed and Sealed this
Twenty-sixth Day of February, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,283,132 B2  
APPLICATION NO. : 11/718149  
DATED : October 9, 2012  
INVENTOR(S) : Günther Fuhr et al.

Page 1 of 1

It is certified that error appears in the above-identified patent and that said Letters Patent is hereby corrected as shown below:

On the Title page at item (73), the assignee information is amended to read as follows:

(73) Assignee: Fraunhofer-Gesellschaft zur  
Foerderung der angewandten  
Forschung e. V., Munich (DE)

This certificate supersedes the Certificate of Correction issued February 26, 2013.

Signed and Sealed this  
Twenty-first Day of May, 2013

Teresa Stanek Rea  
*Acting Director of the United States Patent and Trademark Office*